United States Patent
Chun

(10) Patent No.: US 7,074,396 B2
(45) Date of Patent: Jul. 11, 2006

(54) COMPOSITION AND METHOD FOR PROTECTING BOTH NATURAL AND ARTIFICIAL HAIR COLOR FROM ULTRAVIOLET LIGHT DAMAGE

(75) Inventor: Ho Ming Chun, deceased, late of Belmont, MI (US); by Mary Chun, legal representative, Belmont, MI (US)

(73) Assignee: Access Business Group International LLC, Ada, MI (US)

( * ) Notice: Subject to any disclaimer, the term of this patent is extended or adjusted under 35 U.S.C. 154(b) by 177 days.

(21) Appl. No.: 10/692,318

(22) Filed: Oct. 22, 2003

(65) Prior Publication Data

US 2005/0089483 A1    Apr. 28, 2005

(51) Int. Cl.
  *A61Q 5/00*    (2006.01)
(52) U.S. Cl. .................. 424/70.9; 424/70.1; 424/70.11
(58) Field of Classification Search .................. 424/59, 424/70.1
  See application file for complete search history.

(56) References Cited

U.S. PATENT DOCUMENTS

| | | | |
|---|---|---|---|
| 3,445,566 A | 5/1969 | Skoultchi et al. | |
| 3,661,606 A | 5/1972 | Luethi et al. | |
| 3,808,311 A | 4/1974 | Olson et al. | |
| 3,870,519 A | 3/1975 | Piller | |
| 4,168,302 A | 9/1979 | Schoenberg | |
| 4,585,597 A | 4/1986 | Lang et al. | |
| 4,654,434 A | 3/1987 | Lang et al. | |
| 4,663,088 A | 5/1987 | Lang et al. | |
| 4,668,235 A * | 5/1987 | Evans et al. ................ | 8/115.58 |
| 4,710,584 A | 12/1987 | Lang et al. | |
| 4,726,942 A | 2/1988 | Lang et al. | |
| 4,770,667 A | 9/1988 | Evans et al. | |
| 4,806,344 A | 2/1989 | Gaskin | |
| 4,814,162 A | 3/1989 | Lang et al. | |
| 4,824,602 A | 4/1989 | Juneja | |
| 4,866,159 A | 9/1989 | Forestier et al. | |
| 5,006,331 A | 4/1991 | Gaskin | |
| 5,102,660 A | 4/1992 | Forestier et al. | |
| 5,256,403 A | 10/1993 | Gaskin | |
| 5,380,359 A * | 1/1995 | Honda et al. ................ | 106/414 |
| 5,451,254 A | 9/1995 | Andrean et al. | |
| 5,454,841 A * | 10/1995 | Wolfram et al. ................ | 8/405 |
| 5,597,574 A | 1/1997 | Narayanan et al. | |
| 5,601,811 A | 2/1997 | Gallagher et al. | |
| 5,618,519 A | 4/1997 | Pawelek et al. | |
| 5,633,403 A | 5/1997 | Gallagher et al. | |
| 5,695,747 A | 12/1997 | Forestier et al. | |
| 5,714,136 A | 2/1998 | Yahagi et al. | |
| 5,811,082 A | 9/1998 | Ahlnas et al. | |
| 5,849,274 A | 12/1998 | Gers-Barlag et al. | |
| 5,874,091 A | 2/1999 | Grollier | |
| 5,914,100 A | 6/1999 | Gers-Barlag et al. | |
| 5,948,124 A | 9/1999 | Grit et al. | |
| 5,968,485 A | 10/1999 | Robinson | |
| 5,972,316 A | 10/1999 | Robinson | |
| 5,976,513 A | 11/1999 | Robinson | |
| 6,046,330 A | 4/2000 | Qinghong et al. | |
| 6,060,041 A | 5/2000 | Candau et al. | |
| 6,071,501 A | 6/2000 | Robinson | |
| 6,090,370 A | 7/2000 | Luther et al. | |
| 6,190,645 B1 | 2/2001 | SaNogueira et al. | |
| 6,201,000 B1 | 3/2001 | Luther et al. | |
| 6,224,854 B1 | 5/2001 | Robinson | |
| 6,375,940 B1 | 4/2002 | Richard et al. | |
| 6,428,799 B1 | 8/2002 | Cen et al. | |
| 6,495,122 B1 | 12/2002 | Fankhauser et al. | |
| 6,569,410 B1 | 5/2003 | Fabry et al. | |
| 6,605,577 B1 * | 8/2003 | Harrison et al. ............ | 510/122 |
| 6,620,410 B1 | 9/2003 | Cho et al. | |
| 2002/0034489 A1 | 3/2002 | Wiegland et al. | |
| 2002/0122781 A1 | 9/2002 | Pinzon et al. | |
| 2003/0075709 A1 | 4/2003 | Danielson et al. | |
| 2003/0082126 A9 | 5/2003 | Pinzon et al. | |
| 2003/0148902 A1 | 8/2003 | Coimbra et al. | |

FOREIGN PATENT DOCUMENTS

| | | | |
|---|---|---|---|
| WO | WO 01/05363 | | 1/2001 |
| WO | WO01/05363 | * | 1/2004 |

OTHER PUBLICATIONS

Chedekel M R et al.—"Protection of Hair and Skin from Environmental Damage with Melanin"; Sofw-Journal Seifen, Oele, Fete, Wachse, Verlag fur Chemische Industrie, H. Ziolkowsky K.G. Augsburg, DE, vol. 125, No. 2/3, Mar. 8, 1999, pp. 14, 16-18.

(Continued)

Primary Examiner—Jyothsna Venkat
Assistant Examiner—David Vanik
(74) Attorney, Agent, or Firm—Brinks Hofer Gilson & Lione

(57) ABSTRACT

An improved composition and method for protecting both natural and artificial hair color from the harmful effects of ultraviolet radiation is provided. The composition includes melanin, an ultraviolet absorber, and a cationic surfactant. The composition may also include other ingredients such as additional cationic surfactants, hair conditioning agents, dispersing agents, rheology modifiers, emulsifiers, antioxidants, film formers, and water. A method of protecting hair color from ultraviolet radiation includes applying the composition to natural or artificial hair.

3 Claims, No Drawings

OTHER PUBLICATIONS

Zylepsis and Dragoco—"Sunny nature"; Soap Perfumery Cosmetic, Mar. 1, 2001, XP002316771; http://static.highbeam.com/s/soapperfumeryampcosmetics/march012001/sunnynaturebriefarticle/.

"Pureology"; Soap, Perfumery and Cosmetic, Feb. 1, 2002, XP002316830; http://static.highbeam.com/s/soap-perfumeryampcosticsasia/february012002/pureologyhaslaunchedamanitenancesystemforcolourtre/.

Ciba Pub. No. PC.LE.0212.e.03, 2003.

Dow Corning 929 Cationic Emulsion (Product Information—Ref. No. 22-0266E-01).

Experimental Incroquat UV-283 Anhydrous (Croda MSDS), Jul. 17, 2003, Croda.

FANCORSIL LIM-1, LIM-2, LIM-3 (Fancor specification), Oct. 13, 2003, Fancor.

INCROQUAT UV-283 (DS-127R-5), Oct. 23, 2002, Croda.

INCROQUAT 18MEA-30; Croda MSDS), Croda.

TINOGARD HS PWD (Ciba MSDS No. 1198), May 16, 2001, Ciba.

Gao et al., *Ultraviolet Damage of Natural Gray Hair and its Photoprotection*, Journal of Cosmetic Science, 52 103-118, Mar./Apr. 2001.

http://www.mst.dk/udgiv/publications/2001/87-7944-596-9/html/dap05_eng.htm (Cationic surfactants), Danish Environmental Protection Agency, 2001.

http://www.californiatan.com/product/ingredient_glossary.ehtm, (definition of sodium benzotriazolyl butylphenol sulfonate).

http://www.geocities.com/HotSprings/4266/shampoo.html.

http://www.dongnamchem.com/korea/products/view_products.php?code=db_product&ca, Dongnam Chemical Ind., Ltd., 2000.

http://www.kcpc.usyd.edu.au/discovery/9.5.5-short/9.5.5_cationic.html, Jan. 25, 2001, Key Centre for Polymer Colloids.

http://www.crodausa.com/news.lasso?-token.detail=124&-token.archive=Y, Croda.

* cited by examiner

COMPOSITION AND METHOD FOR PROTECTING BOTH NATURAL AND ARTIFICIAL HAIR COLOR FROM ULTRAVIOLET LIGHT DAMAGE

BACKGROUND OF THE INVENTION

In memory of our friend and colleague, Ho, who loved his work and helped everyone see the joyful things in life.

The present invention relates to a composition and method for protecting both natural and artificial hair color from the harmful effects of ultraviolet radiation and other environmental insults. The composition includes melanin, an ultraviolet absorber, and a cationic surfactant.

The market for hair coloring products is one of the fastest growing markets in the hair care industry today. Human hair fibers are subject to continuous environmental insults including ultraviolet (UV) light. Exposure to UV-B radiation causes the disulfide bonds to photodegrade, resulting in a loss of tensile strength, an increase in the porosity of the hair, and roughening of the cuticle. While UV-B rays damage the cuticle area, UV-A radiation goes deep inside the hair to damage the cortex. One indication of such damage is the disappearance of natural melanin which provides color to the hair. As a result, there is a need for a product that protects artificial, as well as natural hair color.

It has been suggested that melanin and certain benzotriazoles play photoprotective roles (U.S. Pat. Nos. 4,806,344 and 4,668,235), and that quaternary ammonium compounds have UV-absorbing properties (U.S. Pat. No. 5,601,811). While each of these products, individually, may address some of the problems resulting from environmental insults, there is still a need for an effective hair care protectant. The composition of the present invention addresses that need by providing a composition that is believed to have a beneficial protective effect that is greater than the effects of its individual components.

SUMMARY

In general, the composition of the present invention includes from about 0.001% to about 0.5% melanin, from about 0.001% to about 10% ultraviolet absorber, from about 0.001% to about 10% cationic surfactant, or any combination of the above. The combination of these components results in substantially improved color retention for both natural and artificial hair color.

In one embodiment, the present composition includes, in a cosmetically acceptable vehicle, effective amounts of soluble melanin, a benzotriazole derivative, and a cinnamate derivative. The composition may also include other ingredients, such as additional cationic surfactants, hair conditioning agents, dispersing agents, rheology modifiers, emulsifiers, antioxidants, film formers, and water.

Another aspect of the present invention is directed to a method of protecting natural and artificial hair color from environmental insults including ultraviolet light damage. In this aspect, a composition generally including from about 0.001% to about 0.5% melanin, from about 0.001% to about 10% ultraviolet absorber, and from about 0.001% to about 10% cationic surfactant is applied to the hair to achieve the desired effects.

All percentages set forth in the following specification and appended claims are by weight unless otherwise noted.

DESCRIPTION

The present invention provides a composition and a method for protecting both natural and artificial hair color from damage from ultraviolet radiation. The composition of the present invention includes melanin, an ultraviolet absorber, and a cationic surfactant. In one embodiment, the composition includes from about 0.001% to about 0.5% melanin, from about 0.001% to about 10% ultraviolet absorber, from about 0.001% to about 10% cationic surfactant, or any combination of the above. One embodiment of the present invention includes from about 0.01% to about 0.1% soluble melanin, from about 0.01% to about 3% aryl sulfonated benzotriazole, and from about 0.01% to about 3% quaternary ammonium compound.

In another embodiment, the melanin in the present invention comprises a soluble melanin derived from sunflower seed, the ultraviolet absorber comprises a benzotriazole derivative, and the cationic surfactant comprises a quaternized UV absorbing compound. The method of the present invention involves applying an effective amount of the composition of the present invention to hair to achieve the desired effect of protecting both natural and artificial hair color from environmental insults, including ultraviolet radiation.

Melanin is a natural pigment that determines the color of human hair, skin, and eyes. Melanin absorbs ultraviolet light, and this photoprotective role of melanin is related to its physical and biochemical properties. Melanin scatters and degrades radiation to heat, absorbs the radiation and promotes immediate oxidation reaction, and quenches free radicals generated by ultraviolet radiation. Upon exposure to ultraviolet radiation, melanin quenches the formation of damaging free radicals. A general discussion of melanins may be found in Prota, G., "Progress in the Chemistry of Melanins and Related Metabolites," Med. Res. Reviews, 8:525–56 (1988).

Because of the photoprotective properties of melanin, the use of melanin in the present composition contributes to the overall effectiveness of the composition. Further, unlike known sun protectant compositions, the present invention does not require that melanin be combined with ferric chloride and triethanolamine. In one embodiment of the present invention, the melanin comprises a soluble melanin derived from sunflower seed. This type of melanin is commercially available from Zylepsis (Ashford, Kent, UK) under the trade name of MELANEZE.

Melanin is present in an amount from about 0.001% to about 0.5% by weight of the present composition, desirably from about 0.005% to about 0.2%, and even more desirably from about 0.01% to about 0.1%. In one embodiment, the composition includes from about 0.03% to about 0.04% melanin.

Ultraviolet-absorbing compounds are commonly used in products such as sunscreens and tanning lotions. Ultraviolet absorbers may also be used to absorb the ultraviolet rays that damage natural and artificial hair color. Typical examples of ultraviolet absorbers include benzotriazole derivatives, benzophenone derivatives, triazine derivatives, and certain polyoxyalkylenated methine-based compounds, such as those using vanillin and resorcinol as starting materials. A benzotriazole is a compound that has the following structure:

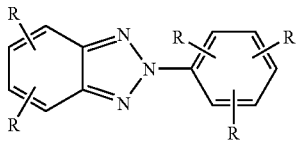

where each R can independently be a hydrogen, a straight alkyl or alkenyl radical group, a branched alkyl or alkenyl radical group, hydroxyl, sulfonate, phosphate, sulfate, alkoxy, carboxylate, or nitro group. Additional ultraviolet absorbers are described in "Sunscreens," Eds. N. J. Lowe, N. A. Shaath, Marcel Dekker, Inc., New York and Basel.

Examples of ultraviolet absorbers for use in the present invention may include benzotriazole derivatives, including aryl sulfonated benzotriazole. A suitable ultraviolet absorber comprises sodium benzotriazolyl butylphenol sulfonate. Sodium benzotriazolyl butylphenol sulfonate is commercially available from Ciba Specialty Chemicals Corporation (High Point, N.C.) under the trade name TINOGARD HS.

In the present invention, the addition of an effective amount of ultraviolet absorber contributes to the protection of both natural and artificial hair from ultraviolet radiation. Unlike known compositions that contain benzotriazole sulfonates, the composition of the present invention does not require that the treatment of hair with benzotriazole sulfonate be under acidic conditions obtained by adjustment with sulfuric acid.

Ultraviolet absorbers comprise from about 0.001% to about 10% of the present composition, desirably from about 0.005% to about 6%, and even more desirably from about 0.01% to about 3%. In one embodiment, the present invention includes from about 0.1% to about 0.15% ultraviolet absorber.

Surfactants are widely used because of their ability to reduce surface tension. Cationic surfactants are characterized by the presence of at least one hydrophobic alkyl chain and a positively charged hydrophilic group. They are typically used in products such as hair conditioners and fabric softeners as antistatic agents or softening/conditioning agents. Two common types of cationic surfactants are long chain amines and quaternary ammonium salts. Quaternary ammonium salts have four substituents on the nitrogen atom and are stable even under extremely basic or acidic conditions.

Specific non-limiting examples of cationic surfactants that may be used in the present invention include cinnamate derivatives, long chain amines, cationic alkyl ammonium salts, and quaternized UV absorbing compounds, including quaternary ammonium compounds such as alkyl quaternary ammonium salts. A suitable cationic surfactant comprises cinnamidopropyltrimonium chloride, which may also perform as a hair conditioner. Cinnamidopropyltrimonium chloride is commercially available from Croda (Parsippany, N.J.) under the trade name INCROQUAT UV-283. In the present invention, the addition of an effective amount of cationic surfactant to effective amounts of ultraviolet absorber and melanin provides a particularly advantageous composition that unexpectedly and surprisingly improves the protection of natural and artificial hair color from ultraviolet radiation.

Cationic surfactants comprise from about 0.001% to about 10% of the present composition, desirably from about 0.005% to about 6%, and even more desirably from about 0.01% to about 3%. In one embodiment, the present invention includes about 1% to about 1.5%.

The novel composition of the present invention may also contain optional hair care benefit ingredients. For example, additional cationic surfactants, hair conditioning agents, dispersing agents, rheology modifiers, emulsions, antioxidants, film formers, and water may also be added to the hair protecting composition.

A suitable antioxidant is a liquid sunflower extract in butylene glycol (25% active). This extract is commercially available from Sederma (Parsippany, N.J.) under the trade name HELIOGENOL. Such additives aid in protecting hair color from fading.

Other examples of optional ingredients include: cinnamidopropyl trimethyl ammonium chloride in dipropylene glycol; lanolinamidopropyl dimethyl ammonium ethosulfate in aqueous butylene glycol; dimethicone copolyol meadowfoamate, commercially available from Fanning Corp. (Chicago, Ill.) under the trade name FANCORSIL LIM-3, which forms dispersions in water and builds viscosity; or cationic emulsions of amine functional silicone polymers, commercially available from Dow Corning (Midland, Mich.) under the trade name Dow Corning 929 Cationic Emulsion, which have film forming properties and improve wet and dry combing ease.

Another aspect of the invention provides a method of protecting natural and artificial hair color from environmental insults such as damage caused by ultraviolet light. The method includes applying an effective amount of the composition of the present invention to hair. In one embodiment, the method comprises applying to hair an effective amount of a composition comprising melanin, an ultraviolet absorber, and a cationic surfactant. The compositional and quantitative variations described above may also be applied to natural or artificial hair to achieve the desired result of protecting the hair from ultraviolet light damage.

The following examples illustrate, but do not limit, the present invention.

EXAMPLE 1

The composition of Table 1 was applied to a hair tress with natural color.

TABLE 1

| Ingredient | Amount |
| --- | --- |
| melanin (MELANEZE (0.50% in propylene glycol)) | 7.58% (0.038% active) |
| UV absorber (TINOGARD HS (0.50% in butylene glycol)) | 22.73% (0.11% active) |
| cationic surfactant (INCROQUAT UV-283) | 1.52% |
| dimethicone copolyol meadowfoamate (FANCORSIL LIM-3) | 2.27% |
| cationic emulsion of aminefunctional silicone polymers (DOW CORNING 929 Emulsion) | 2.27% |
| Water | Q.S. |

A control composition containing only FANCORSIL LIM-3 and DOW CORNING 929 Emulsion in the same percentages as in the test composition, with the balance being water, was applied to a hair tress with natural color.

Each hair tress was continuously exposed to ultraviolet light for ten days. Surprisingly, the hair tress, to which the composition of Table 1 was applied, exhibited 27% less color fading than the hair tress to which the control composition was applied.

EXAMPLE 2

The composition of Table 2 was applied to a hair tress with artificial color.

TABLE 2

| Ingredient | Amount |
| --- | --- |
| melanin (MELANEZE (1% in propylene glycol)) | 3.00% (0.03% active) |
| UV absorber (TINOGARD HS (4.44% in butylene glycol)) | 3.00% (0.13% active) |
| cinnamidopropyl trimethyl ammonium chloride in dipropylene glycol (18.6%) and lanolinamidopropyl dimethyl ammonium ethosulfate in aqueous butylene glycol (13.4%) in butylene glycol | 3.00% (0.96% active) |
| dimethicone copolyol meadowfoamate (FANCORSIL LIM-3) | 3.50% |
| Water | Q.S. |

A control composition containing FANCORSIL LIM-3 in the same percentage as in the test composition, with the balance being water, was applied to a hair tress with artificial color.

Each hair tress was continuously exposed to ultraviolet light for 9.5 days. Surprisingly, the hair tress, to which the composition of the present invention (Table 2) was applied, exhibited 18% less color fading than the hair tress to which the control composition was applied.

EXAMPLE 3

The composition of Table 2 was modified by replacing the melanin with water and adding 0.60% sunflower extract in butylene glycol (HELIOGENOL). This composition was applied to a hair tress with artificial color. The control composition of Example 2 was applied to a hair tress with artificial color.

The hair tress was continuously exposed to ultraviolet light for 9.5 days. The result showed a color retention of only five to six percent more than the control composition. In contrast, as shown in Example 2, the composition according to the present invention exhibited 18% less color fading than did the control composition.

Of course, it should be understood that a wide range of changes and modifications can be made to the embodiments described above. It is therefore intended that the foregoing detailed description be regarded as illustrative rather than limiting, and that it be understood that it is the following claims, including all equivalents, that are intended to define the spirit and scope of this invention.

What is claimed:

1. A composition for protecting natural and artificial hair color from environmental insults comprising:
   a. from about 0.03% to about 0.04% soluble melanin derived from sunflower seed;
   b. from about 0.1% to about 0.15% sodium benzotriazolyl butylphenol sulfonate;
   c. from about 1% to about 1.5% cinnamidopropyltrimonium chloride; and
   d. 3.5% dimethicone copolyol meadowfoamate.

2. The composition of claim 1 further comprising an antioxidant.

3. The composition of claim 2 wherein the antioxidant comprises a liquid sunflower extract in butylene glycol.

* * * * *